United States Patent
Tybinkowski et al.

(10) Patent No.: US 7,020,233 B1
(45) Date of Patent: Mar. 28, 2006

(54) DUAL GANTRY BEARING FOR COMBINED TOMOGRAPHY SCANNER

(75) Inventors: Andrew P. Tybinkowski, Boxford, MA (US); Ronald Swain, Reading, MA (US)

(73) Assignee: Analogic Corporation, Peabody, MA (US)

( * ) Notice: Subject to any disclaimer, the term of this patent is extended or adjusted under 35 U.S.C. 154(b) by 25 days.

(21) Appl. No.: 10/758,313

(22) Filed: Jan. 15, 2004

Related U.S. Application Data

(60) Provisional application No. 60/440,485, filed on Jan. 16, 2003.

(51) Int. Cl.
*G01N 23/00* (2006.01)

(52) U.S. Cl. .................................... 378/4; 250/363.04
(58) Field of Classification Search ............. 378/4–20; 250/363.01–363.1
See application file for complete search history.

(56) References Cited

U.S. PATENT DOCUMENTS

| | | | |
|---|---|---|---|
| 4,797,008 A | 1/1989 | Helbig et al. | |
| 5,071,264 A | 12/1991 | Franke et al. | |
| 5,391,877 A * | 2/1995 | Marks | 250/363.04 |
| 5,448,608 A | 9/1995 | Swain et al. | |
| 5,982,844 A | 11/1999 | Tybinkowski et al. | |
| 6,188,743 B1 | 2/2001 | Tybinkowski et al. | |
| 6,337,894 B1 | 1/2002 | Tybinkowski et al. | |
| 6,865,254 B1 * | 3/2005 | Nafstadius | 378/65 |

* cited by examiner

*Primary Examiner*—Craig E. Church
(74) *Attorney, Agent, or Firm*—McDermott Will & Emery LLP

(57) ABSTRACT

A frame for a tomography scanner system includes a gantry having two, separate annular inner races supported for independent rotation within an annular outer support, wherein the inner races are for respectively supporting x-ray CT scanner components and PET scanner components for rotation with the races about a shared rotation axis of the races within the gantry, and wherein the inner races are spaced along the rotation axis.

15 Claims, 4 Drawing Sheets

DUAL GANTRY BEARING FOR COMBINED TOMOGRAPHY SCANNER

CROSS-REFERENCE TO RELATED APPLICATION

The present application claims priority from U.S. Provisional Patent Application Ser. No. 60/440,485 filed on Jan. 16, 2003, which is assigned to the assignee of the present application and incorporated herein by reference.

FIELD OF THE DISCLOSURE

The present disclosure relates generally to tomography systems and, more specifically, to a combined tomography system. Even more specifically, the present disclosure relates to a dual gantry bearing for a combined tomography system.

BACKGROUND OF THE DISCLOSURE

X-ray computed tomography (CT) scanners have been used for over twenty-five years to create images of cross-sectional slices of subjects, such as human patients, and are particularly used as a medical diagnostic aid. An x-ray CT scanner can produce a 3-dimensional anatomic image of a patient's body, as opposed to just a 2-dimensional image provided by a standard x-ray machine.

An annular gantry normally supports many of the components of an x-ray CT scanner and includes an outer ring secured to a stand and an inner ring mounted for rotation within the outer ring. During a scanning procedure, a patient table is positioned through the center of the gantry, the inner ring is rotated about the table and an x-ray beam is passed through center of the gantry from the spinning inner ring. The components supported by the gantry can include an x-ray tube for providing the x-ray beam, one or more high voltage power supplies, balancing weights, a data acquisition module, and a bank of detectors diametrically opposed from the x-ray source. At least some of these components are secured in the inner ring for rotation therewith.

Positron emissions tomography (PET) scanning is a more recently developed procedure that uses positron emitting radioactive isotopes to show function or metabolism, rather than anatomy as in x-ray CT scanning techniques. A PET scanner is made up of special radiation detectors called scintillators which are arranged in a ring configuration within an annular gantry. Basically, each detector has an associated partner detector oppositely located on the ring. This setup allows for the sensing and measurement of positrons emitted by radioactive isotopes injected into a patient. The measurements are processed through nuclear counting equipment and computers to produce 3-dimensional images that allow quantization of the physiochemical process in the patient's body. PET scanners are used to diagnose and monitor cancer, in addition to diseases of the heart, brain and lungs.

Recently, the results of different types of scanning procedures, e.g., PET and x-ray CT scans (and MRI and x-ray procedures), have been combined, or superimposed, to take advantage of the particular benefits of each procedure. Accordingly, a patient is first scanned using a first procedure, then scanned using a second procedure, and the results of both scans are combined using specialized software and computing systems.

In order to obtain tomographic images of a patient with either scanner, it is necessary that the patient be located exactly at a predetermined position inside the opening of an annular scan gantry of the apparatus. For this reason, such scanners have been provided with a patient handling couch or table which is moveable vertically to be in line with an axis of the scan gantry, and moveable axially in and out of the scan gantry. Some existing systems include a patient support couch or table that is movable between two or more separate scanning machines, such as an x-ray CT scanner and a PET scanner.

What is still desired, however, is a new and improved gantry that supports the components of at least two scanning machines, such as an x-ray CT scanner and a PET scanner. In this manner a patient can be successively scanned by two types of scanning machines by simply repositioning (i.e., moving horizontally) the patient in the same gantry between the components of the two scanning machines.

SUMMARY OF THE DISCLOSURE

The present disclosure generally provides a new and improved gantry that supports the components of at least two scanning machines, such as an x-ray CT scanner and a PET scanner, and, in particular provides a new and improved dual gantry bearing for a combined tomography scanner.

According to one exemplary embodiment of the present disclosure, a frame for a tomography scanner system is provided. The frame includes a gantry having two, separate annular inner races supported for independent rotation within an annular outer support, wherein the inner races are for respectively supporting x-ray CT scanner components and PET scanner components for rotation with the races about a shared rotation axis of the races within the gantry, and wherein the inner races are spaced along the rotation axis.

The foregoing and other features and advantages of the present disclosures will become more readily apparent from the following detailed description of the disclosure, as illustrated in the accompanying drawing.

BRIEF DESCRIPTION OF THE DRAWINGS

Like reference characters designate identical or corresponding components and units throughout the several views.

DETAILED DESCRIPTION OF EXEMPLARY EMBODIMENT

Figure 1:
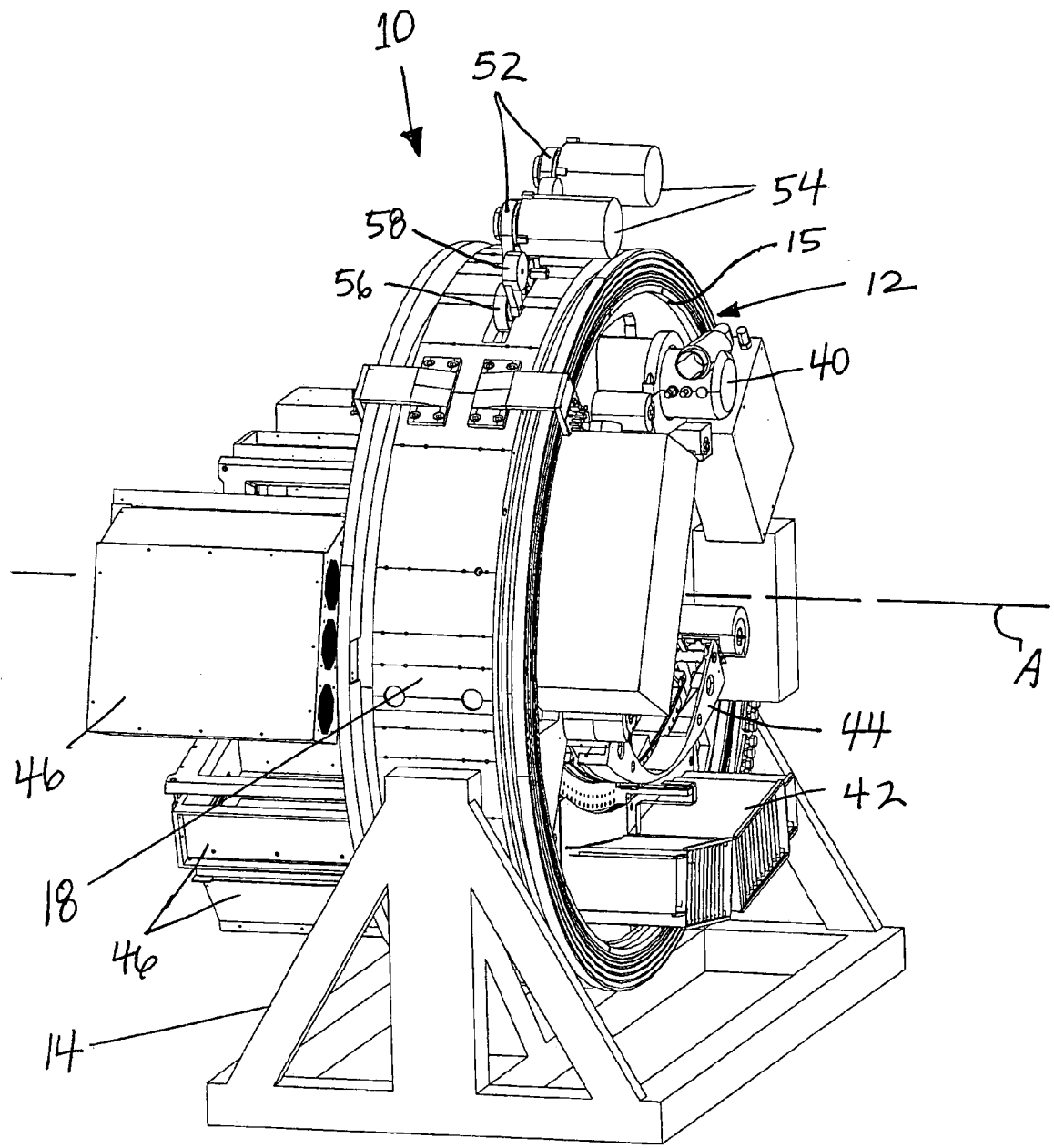
FIG. 1 is a side perspective view of an exemplary embodiment of a combined tomography scanner constructed in accordance with the present disclosure, shown with x-ray CT scanner components and PET scanner components mounted on a gantry thereof.
Figure 2:
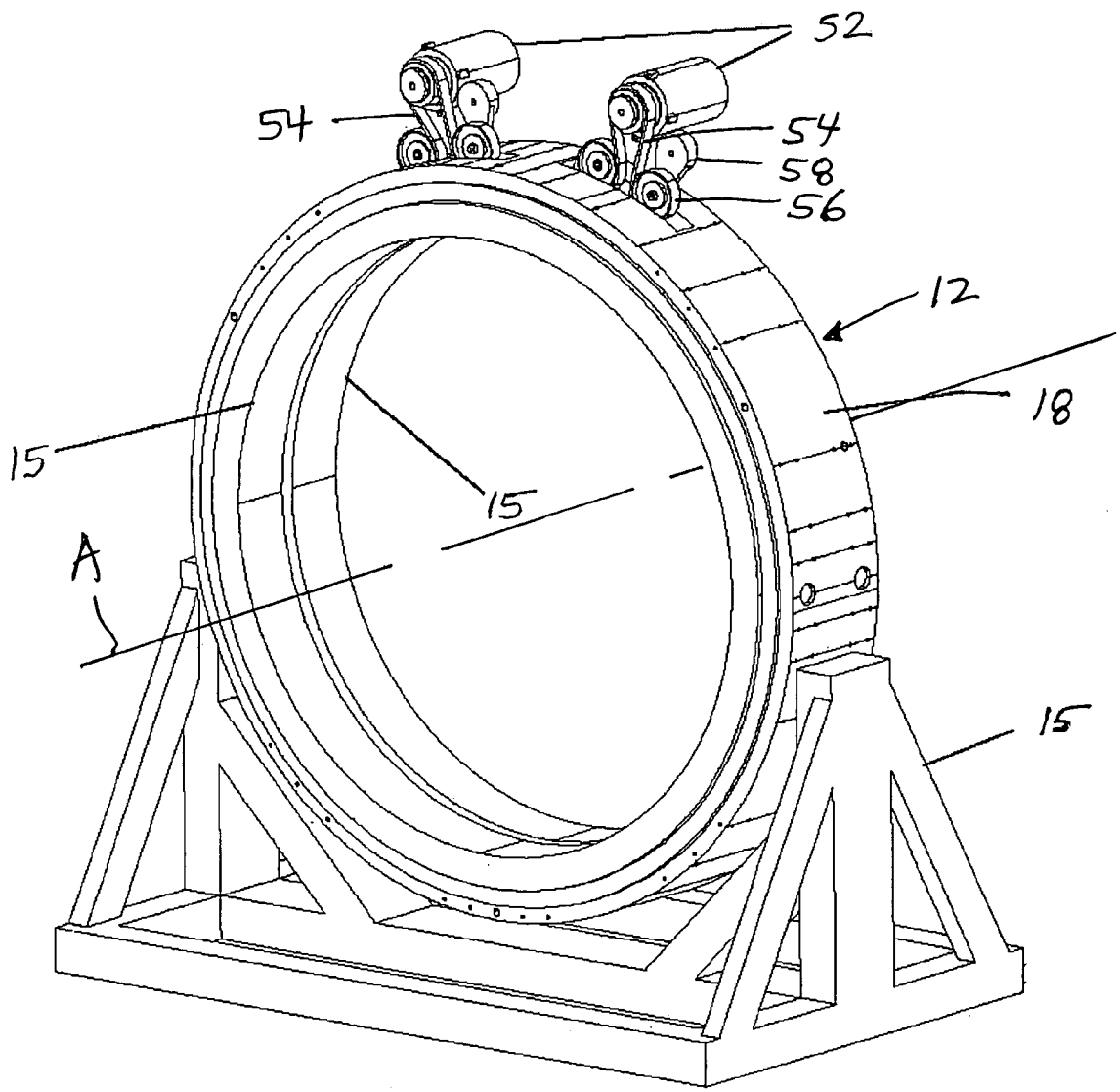
FIG. 2 is a front perspective view of the gantry of the combined tomography scanner of FIG. 1, shown with the x-ray CT scanner components and the PET scanner components removed, and wherein the gantry includes a stand supporting a fixed outer ring, which in turn rotatably supports two inner races (the two races are independently rotatable) and wherein the gantry includes two rotation motors secured to the outer ring and operatively connected to the inner races for turning the inner races.
Figure 3:
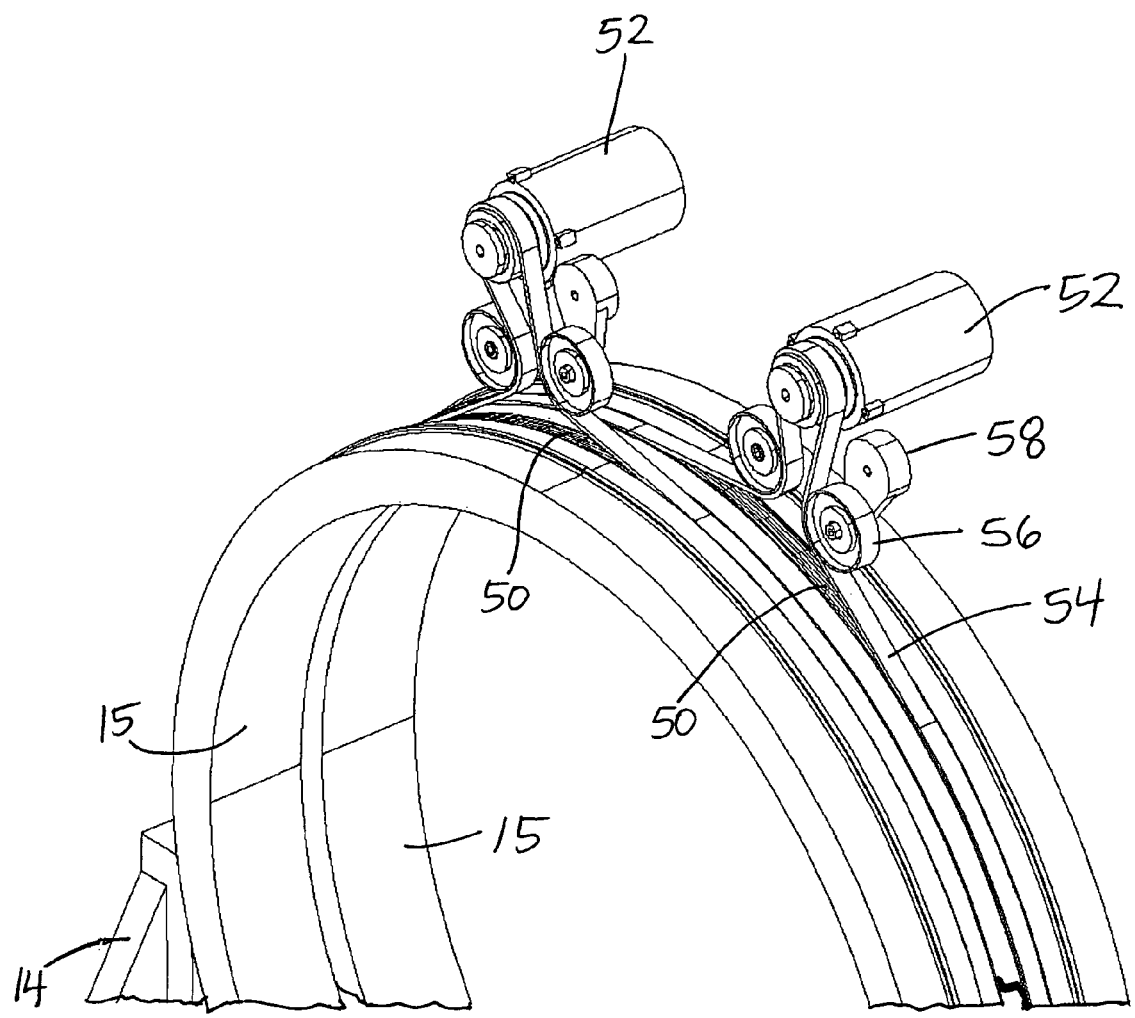
FIG. 3 is an enlarged perspective view of a portion of the inner races of the gantry of the combined tomography scanner of FIG. 1.

Referring first to FIG. 1, an exemplary embodiment of a combined tomography scanner system 10 constructed in accordance with the present disclosure is shown. As also shown in FIGS. 2 through 3, the system 10 includes a gantry 12 supported on a stand 14 and including two, separate annular inner races 15 supported for independent rotation with respect to one another within an annular outer support 18 of the gantry. The inner races 15 respectively support x-ray CT scanner components and PET scanner components, as shown in FIG. 1, for rotation with the races 15.

Figure 4:
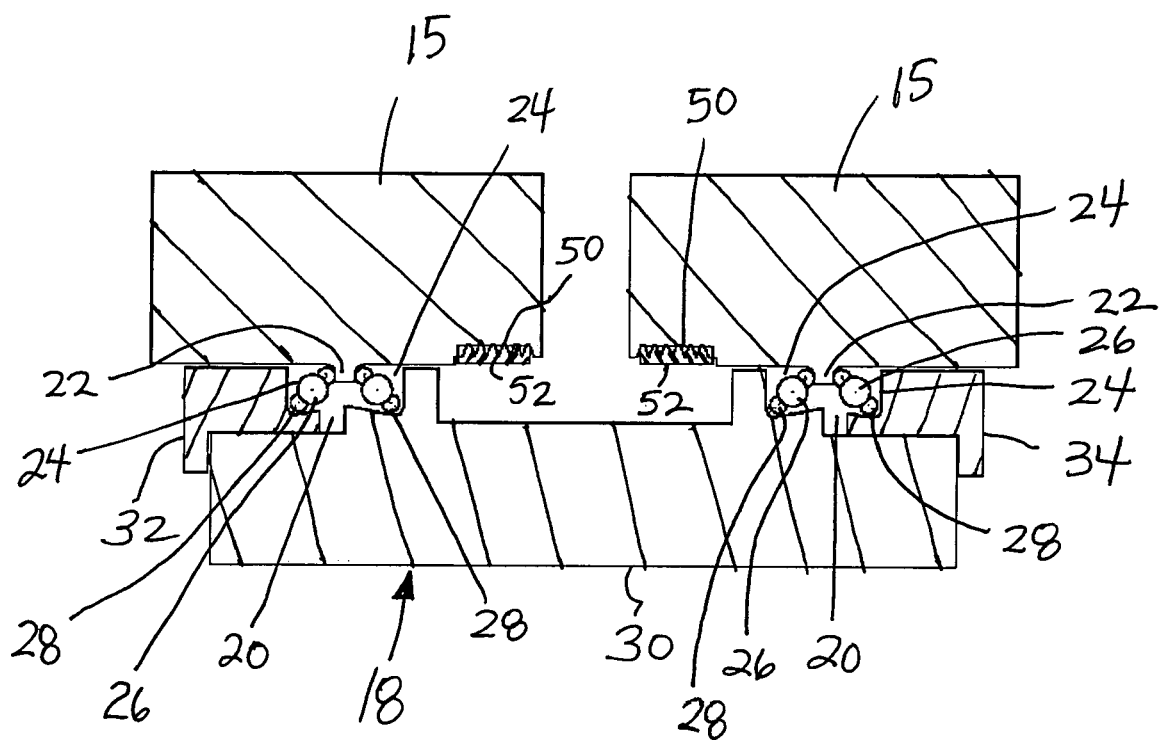
FIG. 4 is an enlarged sectional view of the inner races and the outer ring of the gantry of the combined tomography scanner of FIG. 1, showing exemplary embodiments of rotary bearing assemblies of the gantry.

As shown best in FIG. 4, the annular outer support 18 has radially inwardly facing, continuous circumferencial bearing chambers 20, and the inner races 15 each have a continuous circumferential bearing lip 22 radially extending into the bearing chambers 20 of the outer support 18 to define two circumferential bearing runs 24 within each of the bearing chambers. The gantry 12 also includes roller bearings 26 in the bearing runs 24 allowing the inner races 15 to rotate within the outer support 18, such that the races (and computed tomography components supported on the races) are rotatable about a shared rotation axis "A" (shown in FIGS. 1 and 2) of the races.

Preferably, the roller bearings comprise spherical ball bearings 26. Bearing wires 28 are provided and circumferentially extend within the bearing runs 24 and guide the spherical ball bearings 26. Suspended between the bearing wires 28, the spherical ball bearings 26 glide across the wires with minimal resistance as the races 15 rotate within the outer support 18. In particular, the bearing wires 28 are positioned on either side of the bearing lips 22, and the bearing wires 28 are positioned in two circumferential corners of each of the bearing chambers 20. The bearing arraignment emulates the Franke bearing interface, as disclosed in U.S. Pat. Nos. 4,797,008 and 5,071,264, which are incorporated herein by reference. Ball spacers can be provided between the ball bearings 26 to prevent adjacent balls from contacting or otherwise interfering with each other. The bearings 26 are preloaded according to manufacturer specifications.

A similar bearing arrangement is disclosed in U.S. Pat. No. 6,337,894, to Tybinkowski et al., entitled Rotary Bearing Assembly for CT Scanner Gantry, and which is assigned to the assignee of the present application and incorporated herein by reference. The bearing arrangement confers several advantages. First, the bearings 26 and the wire 28 interface operates with less friction than traditional bearing races as the wires 28 provide a smooth and efficient track for the ball bearings 26. As a result, the bearing arrangement reduces the torque necessary to rotate the inner races 15 within the outer support 18. Also, no custom bearing housing is required, as the bearing runs 24 are provided by the surfaces of the inner races 15 and the outer support 18. Furthermore, the bearing arrangement and novel gantry design according to the present disclosure requires fewer parts, are light weight, operate quietly, and are relatively inexpensive.

The annular outer support 18 preferably is constructed from first, second and third annular pieces 30, 32, 34 axially joined to define the bearing chambers 20. The pieces 30, 32, 34 are secured together with bolts (not shown), which pre-load the bearings 26 and are tightened according to the bearing manufacturer's specifications. Although not shown, the annular first piece 30 can include grease fittings providing communication with the bearing chambers 20 so that the ball bearings 26 can be packed in grease in a convenient manner.

As shown best in FIG. 1, the inner races 15 receive and support tomography scanning components (e.g., an x-ray source 40, an x-ray detector 42, a collimator 44, and scintillators 46) on opposing first and second sides of the gantry 12. The components secured to the inner races 15 will of course rotate with the races 15 about the rotation axis A. The components of one type of tomography scanner, e.g., a CT scanner, are mounted on one of the races 15, while components of a second type of tomography scanner, e.g., a PET scanner, are mounted on the other of the races 15.

The inner races 15 are preferably adapted such that components mounted thereon will be dynamically balanced about the rotation axis A. The term "components" as used herein can include not only one or more of the components listed above, but also any number of elements supported by the inner races 15, depending upon the particular design(s) of the tomography scanners. For example, a number of minor components in the sense of mass and volume, such as a motor driven fan for cooling the x-ray source, anti-scatter plates for the detector array, a detector assembly control panel and/or the like are also typically mounted on the inner races 15, and thus can be included in the term "components" as used herein.

The gantry 12 is also adapted so that the weight of the gantry and any components mounted thereon are substantially aligned with the bearings 26. For example, in the exemplary embodiment shown the bearing lips 22 are positioned equally between ends, i.e., at the middle of, the inner races 15. By locating the bearings 26 at the center of mass of each of the inner races 15, a smaller bearing configuration is allowed since the moment arm between the bearings 26 and the center of mass of the inner races 15 is minimized, thereby decreasing the radial load and thrust load on the bearings. This achieves dynamic balancing of the races 15 relative to the bearings 26, and substantially eliminates cantilevered loading on the bearings.

U.S. Pat. No. 5,448,608 to Swain et al., entitled Tomographic Scanner Having Center of Rotation for All Physics, and which is assigned to the assignee of the present application and incorporated herein by reference, discloses an x-ray tomography system wherein components are mounted on a drum so as to be dynamically balanced for rotation with the drum about a rotational axis. The scanner disclosed by Swain et al. is also configured so that the center of the mass moment of inertia, the center of rotation, the center of thermal expansion of the drum and components mounted thereon, and the center of the scanning plane substantially coincident on the rotational axis of the drum.

Preferably, the outer support 18 and the inner races 15 of the gantry 12 according to the present disclosure are made of the same light-weight, rigid metal such as aluminum, magnesium-aluminum alloy and the like. In the exemplary embodiment of FIG. 4, the inner races 15 are equally spaced (in a direction that is parallel to the axis of rotation A) from a center of the outer support 18 (i.e., midway between ends of the outer support).

Referring to FIGS. 1–4, portions 50 of the radially outermost surface of the rotatable inner races 15 are sheaved to interface with longitudinal grooves of poly-V-belts 52. The cross-sectional V-shaped geometry of the belt 52 in combination with the large circumference of the races 15 serve to minimize belt slippage, and maximizing accuracy in rotational positioning and rotation rate. The sheaved portions 50 are preferably provided adjacent inwardly facing ends of the races 15. For each race 15, the gantry 12 includes a motor 54 and drive pulley system 56 and corresponding belt tensioner 58, such as that disclosed in U.S. Pat. No. 5,982,844 to Tybinkowski et al., which is assigned to the assignee of the present disclosure and incorporated herein by reference.

It should be understood that the embodiments of the present disclosure described herein are merely exemplary and that a person skilled in the art may make variations and modifications to the embodiments described without departing from the spirit and scope of the present disclosures. Because certain changes may be made to the above-described system 10 without departing from the spirit and scope of the present disclosure, all matter contained in the above description or shown in the accompanying drawings shall be interpreted in an illustrative and not a limiting sense. All such equivalent variations and modifications are intended to be included within the scope of this disclosure as defined by the appended claims.

What is claimed is:

1. A tomography scanner system, comprising:
   a gantry including an annular outer support and two, separate annular inner races supported for independent rotation within the annular outer support, the annular support including an annular piece for defining in part two bearing chambers, one for each of the annular inner races, wherein the inner races are spaced along the rotation axis;
   X-ray CT scanner components supported by one of the inner races, and
   PET scanner components supported by the other the inner races.

2. A system according to claim 1, wherein:
   the annular outer support includes two radially inwardly facing, continuous circumferential bearing chambers;
   the inner races each have a continuous circumferential bearing lip radially extending into the bearing chambers of the outer support, wherein each of the bearing lips defines two circumferential bearing runs within each of the bearing chambers; and
   roller bearings are provided in the bearing runs.

3. A system according to claim 2, wherein the roller bearings comprise spherical ball bearings.

4. A system according to claim 3, wherein bearing wires are provided and circumferentially extend within the bearing runs and guide the spherical ball bearings, which are suspended between the bearing wires.

5. A system according to claim 4, wherein ball spacers are provided between the ball bearings.

6. A system according to claim 5, wherein the bearings are preloaded.

7. A system according to claim 6, wherein the annular outer support includes first, second and third annular pieces axially joined to define the bearing chambers.

8. A system according to claim 7, wherein the first, second and third annular pieces are secured together with bolts to pre-load the bearings.

9. A system according to claim 2, wherein the annular outer support includes grease fittings providing communication with the bearing chambers.

10. A system according to claim 2, wherein the bearing lips are positioned equally between ends the inner races.

11. A system according to claim 2, wherein the outer support and the inner races are made of the same material.

12. A system according to claim 2, wherein portions of a radially outermost surface of the rotatable inner races are sheaved, and belts are received in the sheaved portions.

13. A system according to claim 12, further comprising motors operatively connected to the belts for turning the belts and the inner races.

14. A system according to claim 1, wherein roller bearings are provided between the rotatable inner races and the annular outer support.

15. A system according to claim 1, wherein the inner races are equally spaced from a center of the outer support.

* * * * *